US012220476B2

(12) United States Patent
Lee et al.

(10) Patent No.: US 12,220,476 B2
(45) Date of Patent: *Feb. 11, 2025

(54) COMPOSITION FOR CONTROLLED RELEASE OF ACTIVES

(71) Applicant: ELC Management LLC, Melville, NY (US)

(72) Inventors: Wilson A. Lee, Hauppauge, NY (US); Robert Maidhof, Kings Park, NY (US); Danielle Erin Maslin, Setauket, NY (US)

(73) Assignee: ELC Management LLC, Melville, NY (US)

(*) Notice: Subject to any disclaimer, the term of this patent is extended or adjusted under 35 U.S.C. 154(b) by 133 days.

This patent is subject to a terminal disclaimer.

(21) Appl. No.: 17/806,294

(22) Filed: Jun. 10, 2022

(65) Prior Publication Data
US 2023/0398054 A1 Dec. 14, 2023

(51) Int. Cl.
A61K 8/81 (2006.01)
A61K 8/34 (2006.01)
A61K 8/365 (2006.01)
A61K 8/368 (2006.01)
A61K 8/73 (2006.01)
A61Q 19/00 (2006.01)

(52) U.S. Cl.
CPC .......... A61K 8/8147 (2013.01); A61K 8/345 (2013.01); A61K 8/365 (2013.01); A61K 8/368 (2013.01); A61K 8/735 (2013.01); A61Q 19/00 (2013.01); A61K 2800/95 (2013.01)

(58) Field of Classification Search
USPC ....................... 514/54
See application file for complete search history.

(56) References Cited

U.S. PATENT DOCUMENTS

| | | | |
|---|---|---|---|
| 2,949,403 A | 8/1960 | Andreadis et al. | |
| 4,708,865 A | 11/1987 | Turner | |
| 4,803,195 A | 2/1989 | Holzner | |
| 5,374,614 A | 12/1994 | Behan et al. | |
| 5,874,072 A | 2/1999 | Alwattari et al. | |
| 6,171,605 B1 | 1/2001 | Bevacqua et al. | |
| 6,403,109 B1 | 6/2002 | Stora | |
| 6,774,101 B2 | 8/2004 | Stora et al. | |
| 7,223,382 B2 | 5/2007 | Sokolinsky et al. | |
| 7,226,901 B2 | 6/2007 | Stora | |
| 7,323,162 B2 | 1/2008 | Martin et al. | |
| 7,655,613 B2 | 2/2010 | Vlad et al. | |
| 7,682,621 B2 | 3/2010 | Lamberty et al. | |
| 7,794,694 B2 | 9/2010 | Giacomoni et al. | |
| 7,846,889 B2 | 12/2010 | Vlad et al. | |
| 8,343,521 B2 | 1/2013 | Shick et al. | |
| 8,920,787 B2 | 12/2014 | Li et al. | |
| 8,932,570 B2 | 1/2015 | Mu et al. | |
| 9,072,686 B2 | 7/2015 | Bui et al. | |
| 9,078,835 B2 | 7/2015 | Bui et al. | |
| 9,301,910 B2 | 4/2016 | Yontz | |
| 9,535,897 B2 | 1/2017 | Anderson et al. | |
| 10,373,079 B2 | 8/2019 | Lamere et al. | |
| 10,515,400 B2 | 12/2019 | Krishnamurthy et al. | |
| 10,699,321 B2 | 6/2020 | Krishnamurthy et al. | |
| 10,813,874 B2 | 10/2020 | Lee et al. | |
| 11,103,439 B2 | 8/2021 | Lee | |
| 11,129,788 B1* | 9/2021 | Lee .......................... | A61K 8/81 |
| 11,291,618 B2* | 4/2022 | Mohammadi ......... | A61K 8/368 |
| 2003/0082129 A1 | 5/2003 | Buckingham et al. | |
| 2003/0186836 A1 | 10/2003 | Dumanois et al. | |
| 2004/0161435 A1 | 8/2004 | Gupta | |
| 2004/0209795 A1 | 10/2004 | Vlad | |
| 2005/0053567 A1 | 3/2005 | Liu | |
| 2006/0257342 A1 | 11/2006 | Mu et al. | |
| 2008/0286217 A1 | 11/2008 | Chaudhuri | |
| 2011/0073126 A1 | 3/2011 | Mu et al. | |
| 2012/0160258 A1 | 6/2012 | Cruz et al. | |
| 2015/0004115 A1 | 1/2015 | Tan et al. | |
| 2016/0283564 A1 | 9/2016 | Sharon et al. | |
| 2017/0189296 A1 | 7/2017 | SaNogueira et al. | |
| 2018/0075137 A1 | 3/2018 | Lifar et al. | |
| 2018/0369119 A1 | 12/2018 | Lee | |
| 2019/0000382 A1 | 1/2019 | Fitzpatrick | |
| 2019/0179915 A1 | 6/2019 | Yoon et al. | |
| 2020/0155430 A1 | 5/2020 | Lee et al. | |
| 2020/0320112 A1 | 10/2020 | Bansal et al. | |
| 2021/0169769 A1 | 6/2021 | Lee | |
| 2021/0299031 A1* | 9/2021 | Lee ....................... | A61K 8/9789 |

FOREIGN PATENT DOCUMENTS

| | | | | |
|---|---|---|---|---|
| FR | 2954155 B1 | 2/2012 | | |
| FR | 2954152 B1 | 12/2012 | | |
| JP | 2013-121949 A | 6/2013 | | |
| JP | 2014-208636 | 11/2014 | | |
| KR | 10-2009-0114884 | 11/2009 | | |
| KR | 10-2016-0016980 A | 2/2016 | | |
| KR | 10-2019-0036341 A | 4/2019 | | |
| WO | WO 99/13861 | * | 3/1999 | .............. A61K 8/463 |
| WO | WO 2019/074668 A1 | * | 3/2019 | .............. A61K 8/345 |

OTHER PUBLICATIONS

Aculyn 33; Rheology Modifier/Stabilizer A Cost-Effective Thickener for Formulations Containing Polar Solvents; Technical Data Sheet, 2002.

Mintel; GNPD; False Lashes; Record ID: 1961135; Parfums Christian Dior; Parfums Christian Dior; Dior Grand Bal; Colour Cosmetics; Eye Colour Cosmetics—Eye Lash; Japan; Dec. 2012.

Mintel; GNPD; Mascara S302; Record ID: 1513924; Tokiwa Pharmaceutical Co.; Tokiwa Pharmaceutical Co.; Sana Gafixx; Colour Cosmetics; Eye Colour Cosmetics—Eye Lash; Japan; Mar. 2011.

Mintel; GNPD; Record ID: 3127979; Mascara; Pola, Pola, Pola Muselle Nocturnal; Colour Cosmetics; Eye Colour Cosmetics—Eye Lash; Japan; Apr. 2015.

(Continued)

Primary Examiner — Ganapathy Krishnan
(74) Attorney, Agent, or Firm — Peter Giancana

(57) ABSTRACT

Topical film forming compositions that are able to efficiently deliver active ingredients to keratinic surfaces in a timed release manner comprise a combination of acrylates copolymer and acrylates/VA copolymer, and a combination of propane-1,3 diol and glycerin. The sizes of the pores that develop in the dried film may be controlled or fine tuned.

10 Claims, No Drawings

(56) References Cited

OTHER PUBLICATIONS

Mintel; GNPD; Smudgeproof Mascara; Record ID: 3344417; Albion; Technolabo; Paul & Joe Summer 2015; Colour Cosmetics; Eye Colour Cosmetics—Eye Lash; Japan; Jul. 2015.
PCT International Search Report; International Application No. PCT/US2023/068157; Completion Date: Sep. 25, 2023; Mailing Date: Sep. 25, 2023.
PCT Written Opinion of the International Searching Authority: International Application No. PCT/US2023/068157; Completion Date: Sep. 25, 2023.

* cited by examiner

COMPOSITION FOR CONTROLLED RELEASE OF ACTIVES

FIELD OF THE INVENTION

The present invention is in the field of topical preparations for keratinic surfaces. More specifically, the invention pertains to film forming compositions that are able to efficiently deliver active ingredients to the skin, in a controlled release manner.

BACKGROUND OF THE INVENTION

In the following co-owned applications, U.S. Ser. No. 15/632,903 (now U.S. Pat. No. 11,103,439), U.S. Ser. No. 15/906,372 (now U.S. Pat. No. 10,813,874), U.S. Ser. No. 17/029,147, U.S. Ser. No. 17/176,527, U.S. Ser. No. 16/816,995, U.S. Ser. No. 16/197,858, U.S. Ser. No. 16/381,806 (now U.S. Pat. No. 10,507,175), U.S. Ser. No. 16/267,441 (now U.S. Pat. No. 10,980,717), U.S. Ser. No. 17/189,768, and U.S. Ser. No. 16/827,876 (now U.S. Pat. No. 11,129,788), (all incorporated herein by reference in their entirety) the applicant has disclosed specific combinations of acrylates/VA copolymer and acrylates copolymer in an aqueous base, and various useful properties of these combinations depending on the application and the presence of certain other ingredients. Upon application to a skin surface, these compositions, although water based, dry to a film that is clear, flexible and comfortable.

In U.S. Ser. No. 16/267,441 (now U.S. Pat. No. 10,980,717), we disclosed reduced-ethanol perfume compositions that comprise (by total weight of the composition) about 50-60% of water, 3-30% of aromatic ingredients, 4.5-18.5% of acrylates/VA copolymer, 0.25-1.0% of acrylates copolymer, (wherein the weight ratio of acrylates/VA copolymer to acrylates copolymer is in the range of 10:1 to 30:1), one or more plasticizers, which may be up to 4.5% of glycol (butanediol, propanediol, pentylene glycol) or up to 5% alcohol with the proviso that the weight ratio of acrylates/VA copolymer to total plasticizer is in the range of 1:1 to 10:1. It was noted that, in general, more plasticizer in the aqueous phase tends to increase the size of surface pores that develop in the film as the acrylates/VA copolymer—acrylates copolymer composition dries. Controlling this pore size is key to controlling the release of fragrance as a function of time. Compared to the present invention, we note that diffusion of fragrance molecules into the air from aromatic ingredients located in the pores of a dried film is not the same as release of active ingredients from the pores of a dried film into skin, which is driven by osmotic pressure.

In U.S. Ser. No. 16/827,876 (now U.S. Pat. No. 11,129,788), we disclosed spray-on film forming compositions that comprise (by total weight of the composition) about 70-85% of water, 4.7-14% of acrylates/VA copolymer, 0.05-2.5% of acrylate copolymer, 1-5% of plasticizer (which may be any one of glycerin, propanediol, butylene glycol, or combinations thereof). The weight ratio of acrylates/VA copolymer to acrylates copolymer was reported to be in the range 1.8:1 to 280:1, preferably 10:1 to 100:1, more preferably 10:1 to 30:1, and most preferably 20:1. It was reported that the plasticizer has an effect on the porosity of the dried film. It was also reported that when these compositions are applied to a substrate and allowed to dry, the dried film will have an average porosity between 0.25 μm to 3.0 μm. It was further noted that the pore size makes the compositions disclosed therein, useful as a delivery vehicle for active ingredients. In particular, a pore size of 0.9 μm to 2.5 μm is particularly useful for controlled or sustained release of active ingredients. Examples of active ingredients that may be incorporated into the aqueous phase, or an oil phase, were disclosed.

None of the foregoing references discloses the following more robust delivery system for controlled release of actives.

OBJECT OF THE INVENTION

A main object of the invention is to provide a robust delivery system for controlled release of actives that is comfortable on the skin for extended periods of time, that resists contact transfer, but that is easily removed by rubbing under water.

SUMMARY OF THE INVENTION

Topical compositions for controlled release of active ingredients comprise 20% to 60%, by weight, of a combination of acrylates copolymer and acrylates/VA copolymer, wherein the weight ratio of acrylates/VA copolymer to acrylates copolymer ranges from 10:1 to 30:1, preferably 15:1 to 25:1, more preferably about 20:1. The compositions also comprise 5.5%-10%, preferably 6%-7% of a combination of propane-1,3 diol and glycerin, wherein the weight ratio of propane-1,3 diol and glycerin ranges from about 1:1 to about 4:1, preferably from about 2:1 to about 3:1. When these compositions are applied to a substrate, such as the a keratinic surface, and allowed to dry, the dried film will have an average porosity between about 0.1 μm to and 10 μm.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

Throughout the present specification, "film former" or the like refers to a polymer that leaves a film on the substrate to which it is applied, for example, after a solvent accompanying the film former has evaporated, absorbed into and/or dissipated on the substrate.

"Comprise" means that a list of elements may not be limited to those explicitly recited.

Acrylates/VA Copolymer

A first main ingredient of the invention is acrylates/vinyl acetate copolymer ($C_{15}H_{26}O_4$), also known as acrylates/VA copolymer (INCI name), and ethenyl acetate; 2-ethylhexyl prop-2-enoate (IUPAC names); CAS number 25067-02-1. For detailed information, see PubChem Compound Database; CID=168269.

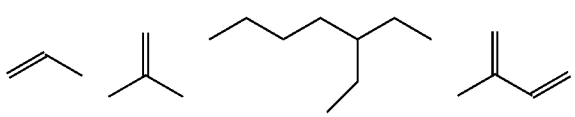

In cosmetics, this tacky material often functions as a binder, film former, adhesive and/or hair fixative. When deployed in aqueous cosmetic systems acrylates/VA copolymer can impart a film on the skin or hair. The pure acrylates/VA copolymer film features a temperature dependence, such that a water rinse of about 38° C. or more will degrade the film, and allow it to be removed from a surface, while retaining its integrity at temperatures at or below normal skin temperature (i.e. 36.5-37.5° C.).

Acrylates/VA copolymer is commercially available, for example, as Vinysol 2140L from Daido Chemical Corp. Vinysol 2140L is a 46.6% aqueous mixture of acrylates/VA copolymer. Vinysol 2140L is reported to have a pH of 4.5, a viscosity of 2,000 mPa-s, a calculated glass transition temperature ($T_g$) of −9° C., while the film exhibits a break elongation of 1,200%, and a break strength of 1.2 MPa (when spread to a thickness 0.1 mm). By itself, the acrylates/VA copolymer is somewhat too rigid for consumer acceptance.

Acrylates Copolymer

To address the problem of high rigidity, the acrylates/VA copolymer was combined with acrylates copolymer, $C_{14}H_{22}O_6$, also known as ethyl prop-2-enoate; methyl 2-methylprop-2-enoate or 2-methylprop-2-enoic acid (IUPAC names); CAS number 25133-97-5. This acrylates copolymer has a lower $T_g$ than acrylates/VA copolymer. For detailed information, see PubChem Compound Database; CID=168299. In various types of cosmetic formulations, acrylates copolymer has a wide variety of uses including as film formers, hair fixatives, binders, and suspending agents, viscosity enhancers, antistatic agents and adhesives.

Acrylates copolymer is commercially available, for example, as Daitosol 5000AD from Daito Kasei Kogyo Co. Daitosol 5000AD is a 50% aqueous mixture of acrylates copolymer. Daitosol 5000AD is reported to have a pH of 5.5-7.5, a viscosity of 50-100 mPa-s, a glass transition temperature ($T_g$) of about −14° C.

Topical aqueous compositions of the present invention comprise a film former that comprises acrylates/VA copolymer and acrylates copolymer in a weight ratio of 10:1 to 30:1, wherein the weight of the acrylates/VA copolymer and acrylates copolymer combined comprise 20%-60% of the weight of the total composition. Preferably the weight ratio of acrylates/VA copolymer to acrylates copolymer is about 15:1 to 25:1, and more preferably about 20:1, such as 19:1 to 21:1. For example, one embodiment of a useful composition comprises 40% acrylates/VA copolymer and 2% acrylates copolymer.

Porosity Adjuster

As so far described, compositions according to the present invention, are water-based, but dry to a porous film upon application to the skin. As the film dries, molecules of the active ingredient(s) accumulate in the pores of the dried film, which prevents a significant amount of agglomeration of the active ingredient(s). This ensures that the size of particles of the active ingredient(s) remain small enough to penetrate the skin. Subsequently, under the action of osmotic pressure, these active molecules are released from the pores of the film, into the skin.

In general, however, there is a need to further adjust the porosity so that the incorporated molecules are not released too slowly or too rapidly. Released too slowly, and the active ingredient may not have a desired effect in the skin. Released too quickly, and the active ingredient is more likely to irritate the skin. We have discovered how to control the release of active materials from the film described above by adjusting the porosity of the film, and doing it without destroying the many useful properties of the film, especially its breathability. By breathability, we mean the air permeability of the dried film. Typically, upon drying, compositions of the present invention have been observed to permit the passage of air even at ambient pressures as low as 1 psi. Maintaining the breathability of the dried film is important for the comfort of the user.

The porosity (or pore size) is controlled by including a porosity adjuster in the composition. The porosity adjuster comprises propane-1,3 diol and glycerin in a weight ratio of about 1:1 to 4:1, and wherein the weight of the propane-1,3 diol and glycerin combined comprise about 5.5% to 10% of the weight of the total composition. Preferably the weight ratio of propane-1,3 diol to glycerin is about 1:1 to 3:1, more preferably 2:1 to 2.5:1. Preferably, the combined weight of propane-1,3 diol and glycerin ranges from about 5.5% to about 7%, more preferably about 6%, by total weight of the composition. For example, a total of 6% porosity adjuster from the combination 4% propane-1,3 diol and 2% glycerin satisfies this requirement.

As noted, we have observed that the sizes of the pores in the dried film may be controlled, or fine tuned, with a combination of propane-1,3 diol and glycerin, as defined above. In general, a greater (lesser) amount of porosity adjuster will result in films with larger (smaller) pores, on average. With the concentrations disclosed above, it is possible to create films in which the average pore size ranges from about 0.1 μm to and 10 μm, and wherein the range of pore sizes about the average can be finely tuned. For example, it is possible to create polymeric films wherein 75%-90% of the pore sizes are within about 1 μm, while the other 10%-25% of pore sizes will be above and below this range. For example, we have created polymeric films according to the present invention wherein about 80% of the pore sizes range from 1.75-2.75 μm, about 10% range from 1.00-1.75 μm, and about 10% range from 2.75-3.75 μm. The larger pores may release active ingredients more quickly than is ideal, but the amount of active ingredient released is relatively small and not likely to cause irritation. Because all or most of the active is captured in pores of similar size (within about 1 μm), the release of most of the active is controllable. If the distribution of pore sizes is too wide, then a controlled release that is suitable for the topical personal care market is less likely to be achieved. In compositions of the invention, it is preferable if 75%-90% of the pore sizes within the dried polymeric film are within about 2 μm, more preferably 1.5 μm, most preferably 1.0 μm.

Active Ingredients

Active ingredients may be incorporated into the aqueous phase or oil phase (if there is one). Non-limiting examples of hydrophilic (water soluble) actives include: algae extract, *Alpinia speciosa* leaf extract, *Alteromonas* ferment extract, ascorbyl acid glucoside (AA2G), *Citrullus lanatus* (watermelon) fruit extract, *Crataegus monogyna* (hawthorn) flower extract, hyaluronic acid, hydrolyzed yeast protein, *Lactobacillus* ferment, *matricaria* (chamomile) extract, *Lens esculenta* (lentil) fruit extract, *Paeonia suffruticosa* (peony) root extract, panthenol, *Pyrus malus* (apple) fruit extract and *Saccharum officinarum* extract. Non-limiting examples of hydrophobic (oil soluble) actives include *Anthemis nobilis* oil, bht (butylated hydroxytoluene), caffeine, *Cocos nucifera* (coconut) oil, salicylic acid, vitamin A, tetrahexyldecyl ascorbate and tocopheryl acetate. Concentration of all active ingredients combined will typically vary between 0.0001% to about 10%, by weight of the composition.

Water

Compositions of the invention are aqueous, and typically comprise at least about 25% of water by weight of the total composition. Preferably, the total amount of water is at least 50%. This amount of water is that from all sources, such as that in Vinysol 2140L and Daitosol 5000AD.

Optional Ingredients

Compositions of the invention may also comprise preservatives as needed, typically up to about 2% by weight of the composition. Also, viscosity modifiers, and/or pH adjusters may be used as needed to create a consumer acceptable product, typically at levels of less than 1% by weight of the composition. At these levels, preservatives, viscosity modifiers, pH adjusters do not seem to adversely affect the controlled release of actives from the dried polymeric film.

Some preferred embodiments of the present invention are single phase aqueous compositions that have little to no oil or silicone. In other preferred embodiments, however, the compositions are lightly emulsified oil-in-water emulsions. The emulsion embodiments are useful when the composition will be used to deliver at least one oil soluble active (such as vitamin E acetate) to a keratinic surface. The emulsion embodiments may comprise one or more surfactants or emulsifiers having an HLB between 8 and 12, and comprise no more than 2% of the total composition, typically between 0.01% to 2% of the total composition.

Agents that significantly interfere with the structure of the dried film may negatively affect the controlled release of actives from the dried polymeric film. Therefore, it is preferred if compositions of the invention comprise a total of no more than 0.5% of structuring agents, for example 0.0001% to 0.5% of structuring agents, such as Carbopol®, wax, clay (such as bentonite) or stearic acid. More preferably, compositions of the invention comprise a total of no more than 0.001% of structuring agents. Most preferably, compositions of the invention comprise no structuring agents. A useful exception to this rule is sodium stearate. Unlike many structuring agents, sodium stearate is partly hydrophilic, which makes it suitable for an aqueous system. Although sodium stearate is partly hydrophobic, its use has not appeared to compromise the objectives of the present invention. This makes it especially useful in embodiments of the present invention when a structuring agent may be needed. Sodium stearate may be used as a structuring agent from 0.0001% to 4% by weight of the total composition. More than that amount will begin to disrupt the acrylic bond strength which may negatively affect the controlled release of actives from the dried polymeric film.

We note that polyurethane tends to make compositions of the invention very rigid, as well as negatively affect the controlled release of actives from the dried polymeric film. Therefore, film forming compositions of the invention comprise no more than 0.5%, for example 0.0001% to 0.5%, of polyurethane. More preferably, compositions of the invention comprise no polyurethane.

Active Delivery

When a composition according to the present invention is applied to a substrate and allowed to dry, the dried film comprises pores in which molecules of the active ingredient accumulate. Thereafter, osmotic pressure drives active molecules out of the pores of the film, and into the skin.

In practice, the porosity of the dried film will be chosen based on the molecular weight of the active material, and on desired rate of release. In general, the greater the molecular weight of an active ingredient, the greater the pore size needed to allow molecules of the active ingredient to accumulate in the pores of the film. The rate of release will be chosen based on the tendency of the active to irritate the skin verses the intended benefit. A slower release rate (smaller porosity) may be required to avoid unacceptable levels of irritation, but too low a release rate may not provide a noticeable benefit. By routine trial and error, a film with a specific pore size profile and release rate can be obtained for each specific active.

For example, in useful compositions according to the present invention wherein the active ingredient was glycolic acid (hydrophilic; molecular weight of 76.05 g/mole), average pore sizes were about 1.5 μm. In other compositions according to the present invention, wherein the active ingredient was salicylic acid (hydrophobic; molecular weight of 138 g/mole), useful average pore sizes ranged from about 1.6 μm to about 3.0 μm. More generally, for molecular weights in the range of about 30 to about 90 g/mole, useful average pore sizes may range from about 0.1 μm to about 1.5 μm. For molecular weights in the range of 90-300 g/mole, useful average pore sizes may range from about 1.5 μm to about 3.0 μm. When the pore size of the dried film is adjusted, based on the molecular weight of the active molecule, then topical compositions according to the present invention exhibit a controlled release of the active ingredient so as to significantly reduce or eliminate inflammation or irritation of the skin. The following examples demonstrates the controlled release of salicylic acid from compositions according to the present invention that comprise 1% salicylic acid.

TABLE 1

|  | Example 1 % | Example 2 % | Example 3 % | Control 1 % | Control 2 % | Blank Skin |
|---|---|---|---|---|---|---|
| Water | 19.05 | 22.05 | 17.05 | 93.00 | 24.05 | — |
| Xanthan gum | 0.20 | 0.20 | 0.20 | 0.00 | 0.20 | — |
| Phenoxyethanol | 0.60 | 0.60 | 0.60 | 0.00 | 0.60 | — |
| Propane-1,3 diol | 4.00 | 2.00 | 5.00 | 0.00 | 5.00 | — |
| Vinysol 2140L | 60.00 | 60.00 | 60.00 | 0.00 | 60.00 | — |
| Daitosol 5000AD | 3.00 | 3.00 | 3.00 | 0.00 | 3.00 | — |
| Alcohol | 3.00 | 3.00 | 3.00 | 0.00 | 3.00 | — |
| Hyaluronic Acid | 1.00 | 1.00 | 1.00 | 0.00 | 1.00 | — |
| Glycerin | 2.00 | 1.00 | 3.00 | 0.00 | 3.00 | — |
| Ucon ™ Fluid | 6.00 | 6.00 | 6.00 | 6.00 | 0.00 | — |
| Salicylic Acid | 1.00 | 1.00 | 1.00 | 1.00 | 0.00 | — |
| Polyquaternium-6 | 0.15 | 0.15 | 0.15 | 0.00 | 0.15 | — |
| pH | 4.20 | 4.11 | 4.09 | 2.73 | 4.43 |  |

Vinysol 2140L - 46.6% aqueous mixture of acrylates/VA copolymer.
Daitosol 5000AD - 50% aqueous mixture of acrylates copolymer.
UCON ™ Fluid - 99.95% PPG-14 butyl ether/0.05% BHT (acts as a solubilizer for salicylic acid).

TABLE 2

| Pore size | | | |
|---|---|---|---|
| | Example 1 | Example 2 | Example 3 |
| Average | 2.24 | 1.61 | 2.89 |
| Median | 2.09 | 1.57 | 2.95 |
| Std Deviation | 0.50 | 0.31 | 0.56 |

TABLE 3

| Migration of Salicylic Acid out of film per hour (measured by fluorescence, arbitrary units) | | | | | | |
|---|---|---|---|---|---|---|
| | Example 1 | Example 2 | Example 3 | Control 1 | Control 2 | Blank Skin |
| 1st hour post application | 1.15 | 2.06 | 3.16 | 2.07 | 0.07 | 0.04 |
| 2nd hour post application | 2.97 | 2.86 | 3.73 | 2.59 | 0.10 | 0.06 |
| 6th hour post application | 4.57 | 4.23 | 4.79 | 3.86 | 0.08 | 0.05 |
| 24th hour post application | 2.43 | 2.17 | 1.41 | 0.85 | 0.07 | 0.05 |

Control 2 and Blank Skin provide a baseline for the fluorescence measurements. As Table 3 shows, there was little migration of salicylic acid from Control 2. Control 2, without the porosity adjuster (i.e. the combination of propane-1,3 diol and glycerin) is an ineffective delivery system for the active ingredient.

In contrast, Control 1 exhibited significant migration of salicylic acid. However, Control 1 has a significantly lower pH and greater cationic charge than Examples 1, 2 and 3 and Control 2. In general, a lower pH and greater cationic charge increase penetration of actives into skin. However, the low pH is not suitable for topical skin products. Thus, examples 1, 2 and 3 according to the present invention provide alternative means of significant active delivery. Furthermore, at 24 hours, there is comparatively little salicylic acid released from Control 1. This is because Control 1 is undergoing free release, in contrast to Examples 1, 2 and 3 which exhibit a controlled release, meaning a more gradual release over time. Based on the standard deviation of migration amounts reported in Table 3, Example 2 gave better results (more controlled release) than Examples 1 and 3.

While particular embodiments of the present invention have been described, it would be obvious to those skilled in the art that various other modifications can be made without departing from the spirit and scope of the invention. Therefore, all modifications that are within the scope of this invention are intended to be covered in the appended claims.

What is claimed is:

1. A topical aqueous composition for controlled release of active ingredients comprising:
    a film former that comprises acrylates/vinyl acetate copolymer and acrylates copolymer in a weight ratio of 10:1 to 30:1, wherein the weight of the acrylates/vinyl acetate copolymer and acrylates copolymer combined comprise 20%-60% of the weight of the total composition;
    a porosity adjuster that comprises propane-1,3 diol and glycerin in a weight ratio of 1:1 to 4:1, wherein the weight of the propane-1,3 diol and glycerin combined comprise 5.5% to 10% by total weight of the composition; and
    one or more cosmetically acceptable active ingredients at a total concentration of 0.0001% to 10%, by weight of the composition.

2. The topical aqueous composition according to claim 1 wherein the active ingredient is salicylic acid.

3. The topical aqueous composition according to claim 1 wherein the active ingredient is hyaluronic acid.

4. The topical aqueous composition according to claim 1 wherein the active ingredient is glycolic acid.

5. The topical aqueous composition according to claim 1 wherein the weight ratio of acrylates/vinyl acetate copolymer to acrylates copolymer ranges from 15:1 to 25:1.

6. The topical aqueous composition according to claim 1 wherein the weight ratio of propane-1,3 diol to glycerin ranges from 1:1 to 3:1.

7. The topical aqueous composition according to claim 1 wherein the propane-1,3 diol and glycerin combined comprise 5.5% to 7% by total weight of the composition.

8. A method of making a delivery system for controlled release of active ingredients, the method comprising the steps of:
    a) providing a topical aqueous composition according to claim 1;
    b) applying the composition to a substrate; and
    c) allowing the composition to dry to a film, such that pores develop in the film,
    wherein the active ingredients accumulate in the pores that develop in the film.

9. The method according to claim 8 wherein the average size of the pores ranges from about 1.5 μm to about 3.0 μm.

10. The method according to claim 8 wherein the average size of the pores ranges from about 0.1 μm to about 1.5 μm.

* * * * *